Jan. 15, 1974 B. J. MACHIN Plant Pat. 3,433
CHRYSANTHEMUM PLANT
Filed Dec. 27, 1971
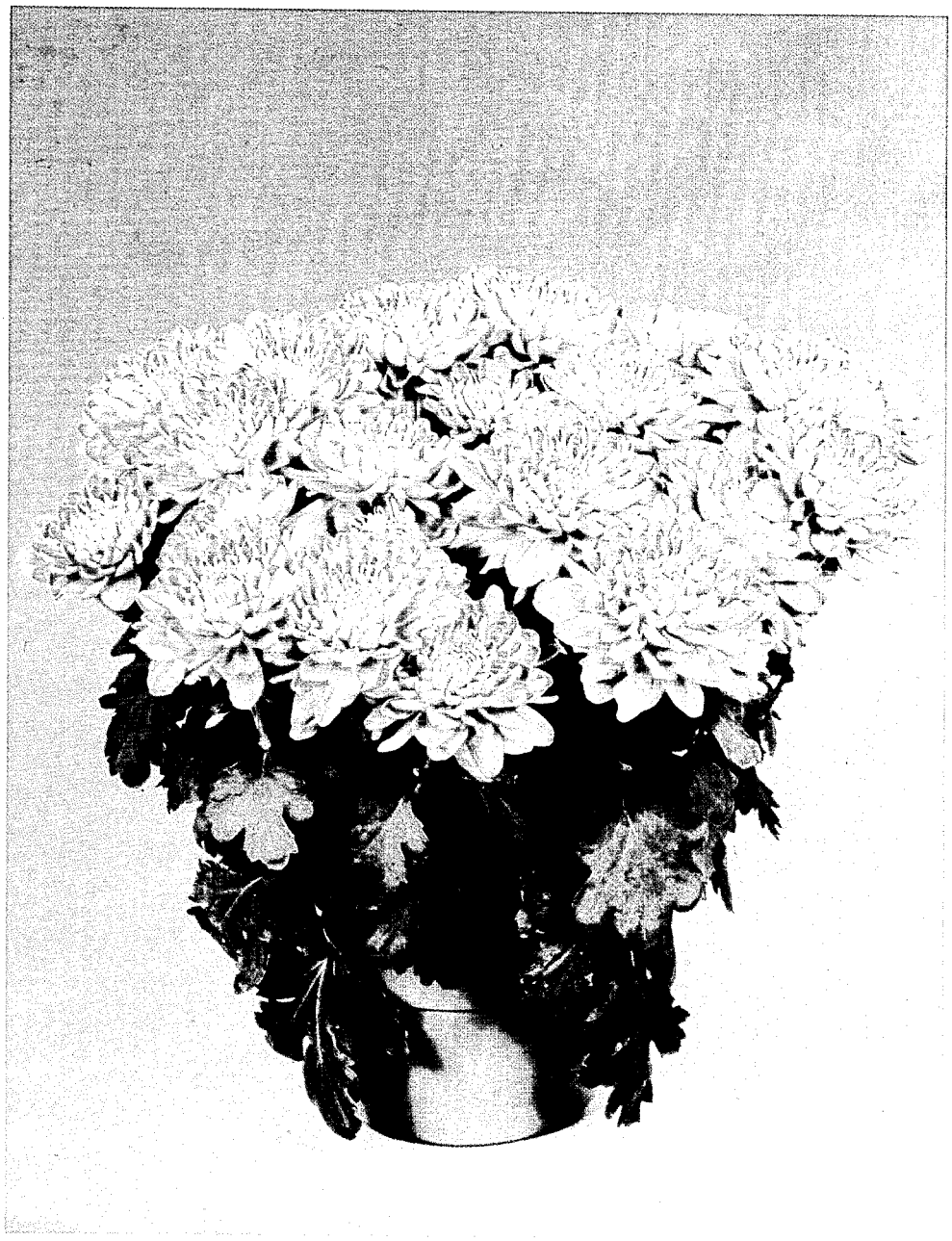

United States Patent Office

Plant Pat. 3,433
Patented Jan. 15, 1974

3,433
CHRYSANTHEMUM PLANT

Barrie John Machin, East Broyle Estate, England, assignor to Frampton's Nurseries Limited, Chichester, Sussex, England Filed Dec. 27, 1971, Ser. No. 212,829
Int. Cl. A01h 5/00
U.S. Cl. Plt.—82 1 Claim This invention relates to a new and distinct variety of *Chrysanthemum morifolium* Bailey, pot type, known as Gay Louise.

Gay Louise is a sport from a seedling known as Louise orignated by me from a cross made in 1966 between the variety Bluebell (unpatented) and the variety Apricot Princess Anne (unpatented), the former being the seed parent, the latter being the pollen parent. The variety Louise resulted from an extensive breeding program with the object of producing improved varieties for year-round pot chrysanthemum production with more uniformity and reduced flowering time compared with existing varieties.

Gay Louise is a sport which occurred in October 1969 by irradiation from the variety Louise, and occurred in cultivated ground at Frampton's Nurseries Ltd., Forbridge Nursery, Runcton, Chichester, England.

Gay Louise is a red bronze sport from Louise which increases the range of color in this family. The bright red bronze color is not at present available in other families of year-round pot chrysanthemums.

Asexual reproduction of this new variety Gay Louise, as performed in Sussex, England, by rooting vegetative shoots, shows that the above characteristics are fixed and come true to type through succeeding generations.

The accompanying drawing shows a typical flower of my new variety depicted in color as nearly true as it is reasonably possible to make the same in a color illustration of this character.

Gay Louise is distinguished from its parent, Louise, by it bright red bronze color, and from both Bluebell and Apricot Princess Anne by its greater uniformity and reduced flowering time. Specifically, Gay Louise is an eight week variety, Bluebell a nine week variety, and Apricot Princess Anne a ten week variety.

As compared with Bluebell, Gay Louise has a flower of firmer texture, and more formally incurving in nature, is more widely branched and produces a more stocky plant. As compared with Apricot Princess Anne, Gay Louise is shorter in habit, gives rise to better shaped plants, and has better petal quality under poor light conditions.

Gay Louise is distinguished over GR Red Anne of the Princess Anne family of pot chrysanthemums, a representative related known variety, in the following particulars:

(1) It is much more responsive and will produce good quality pot plant in 2–3 weeks less growing time round the year.
(2) It is much easier to control height of plant and little or no chemical dwarfing measures are required.
(3) Although flowers are smaller, the form is improved and more flowers per plant are obtained.
(4) Quality of petal is improved in poor winter light conditions.

(5) It is a selection which has been fixed and grows true to type. GR Red Anne is an unstable sport which is constantly re-sporting to various shades of red and bronze.

The following is a detailed description of the new variety Gay Louise with color terminology in accordance with the Royal Horticultural Society Color Chart hereinafter referred to as RHS.

Genus—Chrysanthemum
Species—Morifolium Bailey
Type—Pot
Class—Incurving decorative Breeding: The original variety Louise resulted from a cross between the variety Bluebell and Apricot Princess Anne, the former being the seed parent, and the latter being the pollen parent. The cross was made in 1966 at Frampton's Nurseries Ltd., Forbridge Nursery, Chichester, Sussex, England.

Propagation: Holds its distinguishing characteristics through succeeding propagations by rooting vegetative shoots.

Flower: When grown and observed in Sussex, England, in 3½ inch pots and pinched, up to six flowers per plant are formed—when five plants are planted per 5 inch pots, 4 to 5 flowers are borne on each plant.

Bloom:
*Size.*—Average diameter is 8 cm. when fully open.
*Petalage.*—Decorative with approximately 150 to 200 ray petals and 10 to 20 disc petals.
*Form.*—Incurving decorative.
*Petals.*—Medium length, broad, overlapping, blunt, flat and of thick texture.

Color of open bloom:
Inner face of fully expanded petal, RHS 34B with streaks of RHS 47B.
Outer face of fully expanded petal, RHS 13B.
Inner face of young petal, RHS 35B.
Outer face of young petal, RHS 13A.

Response Group: 8 weeks.
Temperature tolerance: 55–60° F. at night.
Plant: Stocky, well branched habit of growth.

Foliage:
Medium quality.
Average internode length 1½ to 2 cm.
Medium size.
Color RHS 144A.
Medium texture.

Stem:
Thick and strong.
Color, RHS 144C at flowering.

I claim:

1. A new and distinct variety of *Chrysanthemum morifolium* Bailey (pot type), substantially as herein shown and described, characterized particularly as to novelty by its unique combination of a year round response period of approximately eight weeks, its stability as to type, and its red bronze color.

No references cited.

ROBERT E. BAGWILL, Primary Examiner